United States Patent
Ekwall

(10) Patent No.: US 6,591,143 B1
(45) Date of Patent: Jul. 8, 2003

(54) BENDING SENSOR FOR AN IMPLANTABLE LEAD AND A HEART STIMULATOR WITH A LEAD HAVING SUCH A SENSOR

(75) Inventor: Christer Ekwall, Spånga (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/555,085

(22) PCT Filed: Nov. 24, 1998

(86) PCT No.: PCT/SE98/02128
§ 371 (c)(1),
(2), (4) Date: May 24, 2000

(87) PCT Pub. No.: WO99/26693
PCT Pub. Date: Jun. 3, 1999

(30) Foreign Application Priority Data
Nov. 24, 1997 (SE) .............................................. 9704312

(51) Int. Cl.$^7$ ................................................ A61N 1/00
(52) U.S. Cl. ...................... 607/116; 607/17; 607/119; 600/508; 600/587
(58) Field of Search ............... 604/95.04; 607/115–138, 607/17, 19; 600/300, 373–381, 508, 587

(56) References Cited

U.S. PATENT DOCUMENTS

| | | | |
|---|---|---|---|
| 3,815,611 A | * | 6/1974 | Denniston, III |
| 4,461,085 A | * | 7/1984 | Dewar et al. ................. 33/534 |
| 4,600,017 A | | 7/1986 | Schroeppel |
| 4,771,780 A | * | 9/1988 | Sholder ........................ 607/19 |
| 4,784,151 A | | 11/1988 | Frank et al. |
| 4,924,872 A | | 5/1990 | Frank |
| 5,109,842 A | | 5/1992 | Adinolfi |
| 5,261,418 A | * | 11/1993 | Ferek-Petric ................. 607/126 |
| 5,514,171 A | | 5/1996 | Hoegnelid et al. |
| 5,693,074 A | * | 12/1997 | Ferek-Petric |
| 5,933,002 A | * | 8/1999 | Jacobsen et al. |
| 5,978,693 A | * | 11/1999 | Hamilton et al. |
| 6,016,443 A | * | 1/2000 | Ekwall et al. |
| 6,021,350 A | * | 2/2000 | Mathson |
| 6,063,022 A | * | 5/2000 | Ben-Haim ................... 600/41 |
| 6,083,170 A | * | 7/2000 | Ben-Haim ................... 600/463 |
| 6,256,538 B1 | * | 7/2001 | Ekwall |
| 6,264,606 B1 | * | 7/2001 | Ekwall et al. |
| 6,272,371 B1 | * | 8/2001 | Shlomo |

* cited by examiner

Primary Examiner—Mark Bockelman
(74) Attorney, Agent, or Firm—Schiff Hardin & Waite

(57) ABSTRACT

A sensor arrangement, and a heart stimulator employing such a sensor arrangement, identify bending of an electrode lead. A lead which is implantable in a patient is subjected to bending due to movement of the surrounding tissue, and the lead has a deformation sensor therein which emits an electrical signal dependent on the magnitude and orientation of the bending. The deformation sensor can be formed by two parallel channels extending from the tip of the lead within an insulating sleeve of the lead which encloses a conductor element. The channels are filled with an electrically conductive fluid and are connected at their opposite ends to a resistance measuring unit. Bending of the lead causes the resistance of the fluid to change, which is measured by the resistance measuring unit. The channels can be disposed asymmetrically relative to a longitudinal axis of the lead, so that orientation of the bending can also be identified by comparing signals from the respective channels to each other.

12 Claims, 1 Drawing Sheet

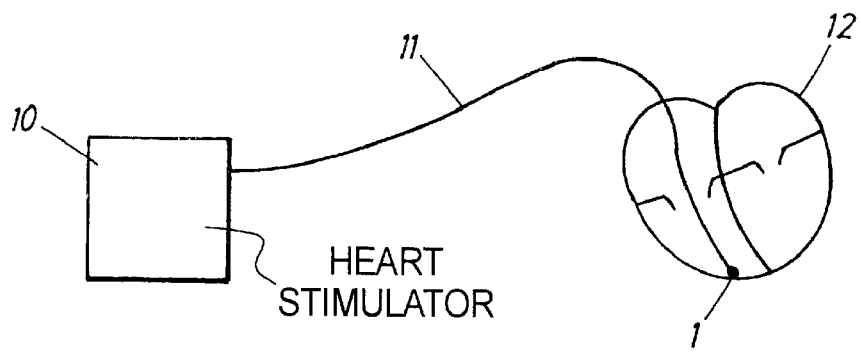
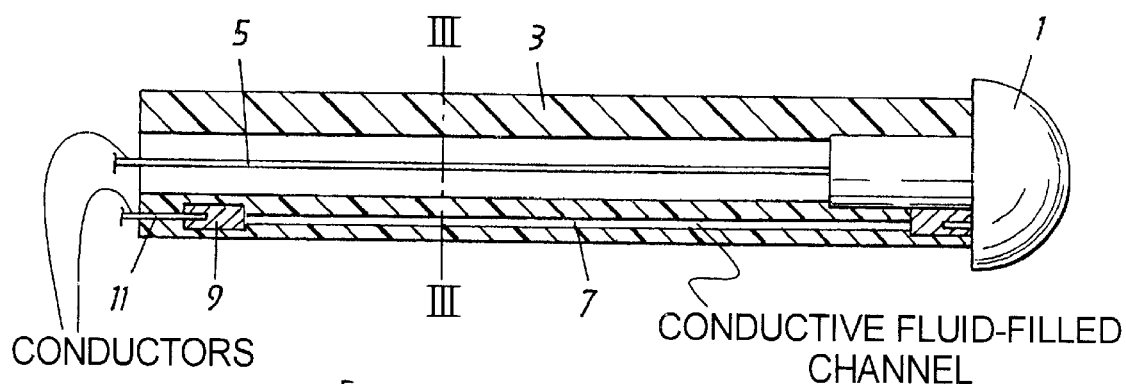
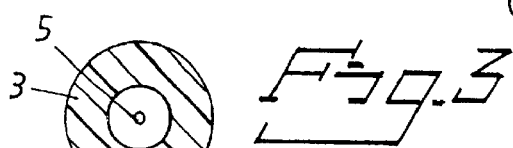
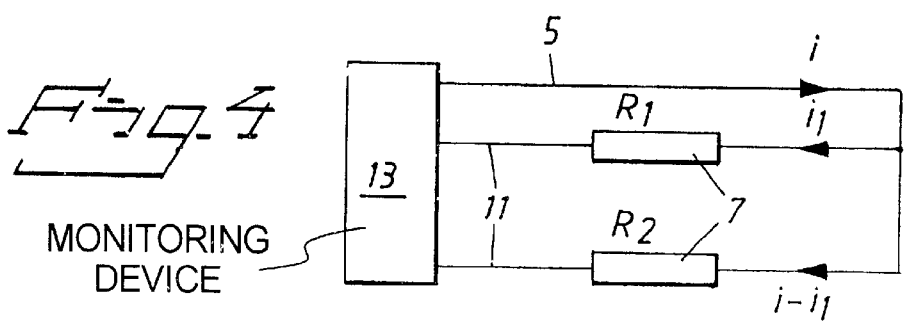

BENDING SENSOR FOR AN IMPLANTABLE LEAD AND A HEART STIMULATOR WITH A LEAD HAVING SUCH A SENSOR

BACKGROUND OF THE INVENTION

1. Field of the Invention

The present invention relates to a sensor for detecting movements of muscle or body tissue, in particular a sensor for an implantable heart stimulator, by means of which the contraction of a heart can be measured and/or determined.

2. Description of the Prior Art

In situations where an implanted stimulator is used, it is normally important to detect the muscular contraction of the stimulated muscle. For example, in the case of a pacemaker the heart contraction is of special interest. Heart contractions may generally have different origins and hence differ significantly from each other as to their characteristic shape or dependence of time. They may be normal, thus triggered by the internal conduction or "nervous" or purkinje system of the heart, stimulated or of type extra contraction (extra systole; VES, SVES or PVC). In sensing heart contractions by means of electrical measurements stimulation polarization potentials and muscular movement interference can create noise virtually making the measurements impossible. In these cases, a device sensitive to the mechanical contraction of the contraction of the stimulated, would confirm and improve the function of a heart stimulator.

In some situations it would be of interest to know also the efficiency of the stimulation or the direction of the stimulation propagation in order to improve the stimulation device or method, such as improving the stimulation algorithm. Examples of such cases are where a differentiation is wanted or required between conducted (normal) contraction and stimulated contraction of the heart (Autocapture), where a differentiation is wanted between normal conducted contraction and extra systole and where ischemia is to be detected. In those cases the change of contraction propagation in the heart muscle will be different, since the propagation pattern or the direction of the contraction movement will be different. For example, in cardiac ischemia, a portion of the heart wall or heart muscle suffers from an insufficient oxygen supply. This means that a propagating depolarization and thus the contraction cannot pass this portion or at least is subject to a delayed conduction and thus contraction. As a result, alternative propagation paths are favored, causing a change in the movement pattern. In order to detect such types of pathological changes so that they can be taken into account when stimulating or monitoring the heart function, a device is needed which is capable of sensing differences in the movement pattern.

Known methods of sensing heart contraction include:

Intracardiac Electrographic Monitoring (IEGM), which does not always reflect the actual contraction activity as already indicated above, owing to the electrical measurement made. The measurement can thus be disturbed by other electrical signals such as from muscular activity and polarization. Direction, changes of movement pattern or generally the character of the contraction cannot be determined. The measurement only provides information about the changes that occur in a close vicinity of the site of the sensing electrode.

Systolic pressure sensing gives information on the contraction and possibly also the efficiency thereof. It is usually not significantly affected by other body movements and is not affected by electrical signals. However, it cannot detect the propagation direction or changes in the movement pattern.

Measuring by means of an accelerometer. This method senses only contraction forces thus does not sense the propagation direction or changes in the movement pattern.

Measuring using ultrasonic waves. No implantable device is available. The current consumption for making the measurements is too high.

Measuring the impedance of the heart. This could be done for example between an electrode and the pacemaker housing. However, it can sense only changes of the heart volume. In U.S. Pat. No. 5,514,171 a pressure and heart movement sensor of the systolic pressure sensing type is disclosed. An electric quantity is measured between two electrical conductors in the electrode cable. In one embodiment, see FIG. 2, a sensor medium such as an electrolyte is enclosed in an elongated cavity having elastic walls. The cavity is formed by a widened portion of an elastic tube, which in its other portions has a smaller diameter only enclosing a centrally disposed electrical conductor. The impedance is measured between two conductive plates located at each end of the cavity, the impedance varying in dependence of the pressure of the ambient medium where the sensor cavity is placed. It is not described how this sensor cavity and associated conductors can be incorporated in an electrode lead for a heart stimulator. Other systolic pressure sensors are disclosed in U.S. Pat. Nos. 4,784,151, 4,924,872 and 4,600,017.

It is an object of the invention to provide a sensing device that can be incorporated in an electrode lead for an implantable stimulator and is capable of detecting movements of the surrounding tissue where it is placed, in particular movements of the heart muscle.

It is another object of the invention to provide a sensing device for sensing tissue movements that is not affected by the environment or any electrical phenomena in the tissue.

It is another object of the invention to provide a sensing device that is capable of sensing the orientation of movements of the surrounding, where the sensing device is placed, in particular the orientation of a contraction caused by a depolarization propagating in a muscle such as the heart muscle.

The problem that is solved by the invention is thus to provide a sensor that can be built into for example an electrode lead for a heart stimulator, that is substantially unaffected by electrical signals from muscle activity and signals originating from stimulation and that can detect movements of body tissue, in particular the orientation of movements and changes of movement patterns.

The above object is achieved in accordance with the principles of the present invention in an arragement having a deformation sensor for measuring or detecting the bending of an elongated body in which the deformation sensor is placed, the body preferably being an electrode lead which is part of an implantable system adapted for muscular or neuron stimulation in a living being, in particular a heart stimulator, the body thus e.g. being an electrode lead included in the electrode system of a heart stimulator. In practice, the tip end of such an electrode lead is positioned in contact with the muscle to be stimulated, i.e. in the preferred case with the heart. The end portion of the lead is placed to have an arched or curved configuration so that the tip end will maintain its contact with the tissue in order to coop with growth, movements and stretching of the living being in which the electrode lead is arranged. When the muscle contracts and thus is becoming thicker, the bending radius of the lead end portion will be lower and thus the curvature thereof larger.

The deformation sensor can be any known type capable of providing some electrical signal responding to a bending movement of the sensor and of the material to which the sensor is attached. For example, it is possible to use a device containing an electrically conducting material that is arranged so that it changes its electrical characteristics when it is subjected to bending. One such device contain resistance elements that changes their resistance when deformed, such as strain gauges. The resistance element is then attached to some suitable flexible body that follows the movement of the medium or tissue where it is placed.

By attaching two such detector elements in one electrode lead at asymmetrical positions in the lead, in addition the orientation of the bending movement can be sensed. Since a lead normally is elongated and/or cylindrical, the term asymmetrical for the case of two detector element means that the detector elements are not placed at diametrically opposed locations, i.e. not in the same plane extending through the longitudinal axis of the body. Preferably, they are instead located in planes through the longitudinal axis, which form an angle of 30°–150° to each other, the angle preferably being essentially equal to 90°. The detector elements should also be located at or in the same longitudinal region of the lead in order to provide information on the bending movement. Such an arrangement of two mechanical detector elements can thus be generally used in order to obtain valuable information on bending directions. In the case where more than two detector elements are used, at least one pair of detector elements should have the asymmetrical position as described above.

A resistor element used as the deformation sensor is formed by a channel in the lead body, extending in the longitudinal direction thereof. The body can be an electrically isolating sleeve surrounding a central electrical conductor and then the channel is located in the material of the sleeve, the sleeve having the same uniform inner and outer diameter also at the region where the channel is made. The channel is filled with an electrically conductive fluid, such as a suitable electrolyte, e.g. a salt diluted in water, preferably a saline solution being biologically inert to body fluid. Terminals are electrically connected to the ends of the channel for connection to circuitry for the resistance of the fluid between the ends of the channel. The fluid is thus located in a closed cavity. When the lead is subjected to a bending movement, the cavity changes its shape, in particular its diameter, and then also the resistance of the enclosed fluid changes. Such a device could generally also be sensitive to the ambient pressure, see U.S. Pat. No. 5,514,171 discussed above, but by using a substantially incompressible fluid, i.e. a fluid which does not change its volume significantly when subjected to the pressures existing at the place where the sensor is intended to be used, a change of the ambient pressure will not influence the resistance of the enclosed amount of fluid.

DESCRIPTION OF THE DRAWINGS

FIG. 1 is a schematic illustration of a heart stimulator with an electrode lead inserted into a heart, in which the inventive deformation sensor can be used.

FIG. 2 is a cross-sectional view of an electrode lead for a heart stimulator of the type shown in FIG. 1, having an inventive deformation sensor disposed close to the tip of the lead, the section being taken in the longitudinal direction of the lead.

FIG. 3 is a cross-sectional view of the electrode lead of FIG. 1, taken perpendicularly to the longitudinal direction of the lead, as indicated by the section line III—III of FIG. 2.

FIG. 4 is a block diagram of an electrical circuit for use in an arrangement incorporating the deformation sensor in accordance with the invention.

DESCRIPTION OF THE PREFERRED EMBODIMENTS

In FIG. 1 a heart stimulator 10 with an electrode lead 11 comprising a tip electrode 1 is shown. The proximal end of the electrode lead is attached to the heart stimulator 10 and the distal part of the electrode lead is inserted into a heart 12.

In FIG. 2 the end portion of an electrode lead or cable for a heart stimulator according to a preferred embodiment of the invention is shown. It has a tip electrode 1 at the end of the lead, the tip being made of an inert, electrically conducting material. The tip 1 is attached to a flexible lead sleeve 3 made of a flexible, electrically insulating material such a suitable polymer, normally silicon. The outer diameter of the electrode lead is in the range of 1–3 mm, preferably 2 mm. Inside the sleeve 3 extends centrally an electrically conducting wire 5, e.g. a helically wound, which is attached to the tip electrode 1 for providing an electrical heart stimulation pulse thereto. The insulating sleeve 3 has a rather thick wall, preferably less than 1 mm.

In the wall of the sleeve 3 at least two parallel channels 7 extend from the tip 1 and have a length of a few centimeters. Each of the channels 7 ends at a channel connector 9, located in the wall of the sleeve 3. From each channel connector extends an electrically conducting wire 11 embedded in the wall of sleeve and electrically isolated from the other conducting wire and the tip conductor 5, up to a monitoring device 13 (in FIG. 4) in e.g. a heart stimulator. The channels 7 have a generally straight configuration. As is seen in the transversal cross-section of FIG. 3, in the preferred case of two channels 7, they are located asymmetrically and advantageously at an angular interval from each other, that is substantially 90°, as taken in regard of the longitudinal axis of the electrode lead. According to an alternative embodiment of the invention the channels can be placed anywhere along an electrode lead and thereby enabling measurements at any site along the lead.

The channels 7 are filled with an incompressible, electrically conducting fluid, e.g. an electrolyte such as a saline solution comprising 0.9% NaCl which is compatible and isotonic with the fluids of the human body. An electrical current can be conducted from the monitoring device 13 through the tip conductor 5, the tip 1, the conducting fluid in one of the channels 7, the respective connector device 9 and conductor 11 back to the monitoring device. The electrical resistance of this conductive path is measured and evaluated. When the end portion of the electrode lead is bent, the diameters of the channels change and they can be widened or narrowed depending on the orientation of the bending. If the conductive fluid is assumed to be incompressible, the volume of the channels will be constant and then at the inner side of the bending, at its concave side, a channel located there will have its cross-sectioned widened, and at the outer side of the bending, at the convex side of the bending, a channel located there will have its cross-section narrowed. The isolating sleeve should be rather rigid so that is not sensitive to pressure changes in the medium surrounding the electrode lead.

The resistance of the electrically conductive fluid in a channel 7 between the tip electrode 1 and its connector device will thus change for a bending of the lead and the change will also depend on the orientation of the bending. The monitoring device 13 measures the resistance changes and can therefrom calculate the amount of bending i.e. produce some measure of the bending angle. Further, by comparing the changes of resistance of the loops comprising the two channels 7 to each other it can determine the bending orientation.

In FIG. 4 a block diagram shows an equivalent electrical circuit of the sensor according to the invention. The monitoring device 13, preferably placed in a heart stimulator, is connected to the two channels 7, having a resistance $R_1$, $R_2$, respectively. A measurement current I is applied to the channels 7 via the electrical tip conductor 5. According to Ohm's law the relationship then equals $I/I_1-1$ where $I_1$ is the current through $R_1$. The monitoring device measures $I_1$ and $R_1/R_2$ is thus easily determined and used to determine the amount of bending and the bending orientation as indicated above.

The applied measurement current I is chosen to a value well below the current used for stimulation, which in pacemakers of today is in the order of 1–10 mA. A preferred range for the measurement current is 1–10 $\mu$A, preferably 2–6 $\mu$A, and the current can be applied both as AC and DC.

The bending measurement can be performed during the whole heart cycle or only during a specific time window that is started after an intrinsic heart event or an applied heart stimulation pulse (in the atrium or in the ventricle). The length of the time window can be optionally chosen. If bending should be measured related both to the depolarization and repolarization of the heart tissue, the time window is chosen to approximately 300 ms or if bending related only to depolarization should be measured a time window that is only about 100 ms is required.

Although modifications and changes may be suggested by those skilled in the art, it is the intention of the inventor to embody within the patent warranted hereon all changes and modifications as reasonably and properly come within the scope of his contribution to the art.

I claim:

1. An arrangement for detecting movements of living tissue comprising:
    a lead adapted for implantation in living tissue which causes said lead to be subjected to bending with an associated orientation, said lead containing at least one electrical conductor; and
    a deformation sensor in said lead which is deformed by said bending of said lead and which emits an electrical signal dependent on a magnitude of said bending of said lead and which identifies the associated direction of said bending of said lead.

2. An arrangement as claimed in claim 1 wherein said lead has a longitudinal axis, and wherein said deformation sensor comprises at least two separate deformation sensing elements disposed within a common longitudinal region of said lead and disposed asymmetrically relative to said longitudinal axis.

3. An arrangement as claimed in claim 2 wherein two of said separate sensing elements are disposed offset from each other by an angle relative to said longitudinal axis, said angle being in a range between 30° and 150°.

4. An arrangement as claimed in claim 3 wherein said angle is substantially equal to 90°.

5. An arrangement as claimed in claim 1 wherein said deformation sensor is formed by a channel, having opposite ends, filled with an electrically conductive fluid which changes resistance dependent on said bending of said lead, and a resistance measurement unit electrically connected to said opposite ends of said channel for measuring said resistance of said fluid.

6. An arrangement as claimed in claim 1 wherein said deformation sensor comprises first and second parallel channels within said lead, each of said first and second channels having opposite ends and each of said first and second channels being filled with an electrically conductive fluid which changes resistance dependent on said bending of said lead, and a resistance measurement unit electrically connected to the opposite ends of said first channel and electrically connected to the opposite ends of said second channel for measuring changes in the resistance of the fluid in the respective first and second channels.

7. An arrangement for detecting movements of living tissue comprising:
    a lead adapted for implantation in living tissue which causes said lead to be subjected to bending, said lead having a longitudinal axis;
    at least one electrical conductor within said lead; and
    a deformation sensor in said lead for detecting a mechanical property at a localized region of tissue surrounding said lead, said deformation sensor comprising at least two identical sensor elements disposed in said lead for detecting said mechanical property within a common plane perpendicular to said longitudinal axis, and disposed to detect said mechanical property in respective regions of said tissue disposed asymmetrically relative to said longitudinal axis.

8. A sensor arrangement for detecting movements of living tissue, comprising:
    a lead adapted for implantation in tissue which causes bending of said lead, said lead comprising an electrically insulating sleeve and at least one electrical conductor enclosed in said sleeve; and
    a deformation sensor for generating an electrical signal dependent on said bending of said lead, said deformation sensor being formed by at least first and second channels in said sleeve, said first and second channels each having opposite ends and each being filled with an electrically conductive fluid which changes resistance dependent on said bending of said lead, and a resistance measurement unit electrically connected to said ends of said first channel and said ends of said second channel for measuring changes in said resistance of said fluid in each of said first and second channels.

9. An implantable heart stimulator comprising:
    a housing adapted for implantation in living tissue and containing an electrical stimulation source;
    an electrode lead electrically connected to said electrical stimulation source and adapted for implantation in said tissue for delivering electrical stimulation to said tissue, said lead being subjected to bending with an associated orientation due to movement of said tissue; and
    deformation sensor ins aid lead which emits an electrical signal dependent on a magnitude of said bending of said lead and which identifies the associated direction of said bending of said lead.

10. An implantable heart stimulator as claimed in claim 9 wherein said electrode lead has a tip disposed remote from said electrical stimulation source, and wherein said deformation sensor is disposed at said tip of said lead.

11. An arrangement as claimed in claim 10 wherein said deformation sensor is formed by a channel, having opposite ends, filled with an electrically conductive fluid which changes resistance dependent on said bending of said lead, and a resistance measurement unit electrically connected to said opposite ends of said channel for measuring said resistance of said fluid, said tip forming one electrical connection between an end of said channel and said resistance measurement unit.

12. An arrangement as claimed in claim 10 wherein said deformation sensor comprises first and second parallel channels within said lead, each of said first and second channels having opposite ends and each of said first and second channels being filled with an electrically conductive fluid which changes resistance dependent on said bending of said lead, and a resistance measurement unit electrically connected to the opposite ends of said first channel and electrically connected to the opposite ends of said second channel for measuring changes in the resistance of the fluid in the respective first and second channels, said tip forming one electrical connection between one end of said first channel and one end of said second channel and said resistance measurement unit.

* * * * *